US012478495B2

(12) United States Patent
Friederich et al.

(10) Patent No.: US 12,478,495 B2
(45) Date of Patent: Nov. 25, 2025

(54) TRUNK EXOSKELETON

(71) Applicant: The United States Government as represented by the Department of Veterans Affairs, Washington, DC (US)

(72) Inventors: Aidan Friederich, Cleveland Heights, OH (US); Ronald J. Triolo, Cleveland Heights, OH (US); Musa Audu, Shaker Heights, OH (US)

(73) Assignee: THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 359 days.

(21) Appl. No.: 17/973,605

(22) Filed: Oct. 26, 2022

(65) Prior Publication Data

US 2023/0127834 A1 Apr. 27, 2023

Related U.S. Application Data

(60) Provisional application No. 63/271,917, filed on Oct. 26, 2021.

(51) Int. Cl.
*A61F 5/02* (2006.01)
*A41C 1/14* (2006.01)
(Continued)

(52) U.S. Cl.
CPC ................ *A61F 5/028* (2013.01); *A41C 1/14* (2013.01); *A61F 2005/0165* (2013.01);
(Continued)

(58) Field of Classification Search
CPC .............. A61F 5/028; A61F 2005/0165; A61F 2005/0179; A61F 5/02-03; A41C 1/02; A41C 1/08; A41C 1/12; A41C 1/14; A41C 1/16; A41C 1/18; A41C 1/20; A41C 3/12; A41C 3/122; A41C 3/124; A41C 3/128; A61H 3/00; A61H 3/008; B25J 9/0006;
(Continued)

(56) References Cited

U.S. PATENT DOCUMENTS 2,181,689 A * 11/1939 Bell ........................ A61F 5/028 602/19
5,188,586 A * 2/1993 Castel ................ A41D 13/0525 128/845
5,651,764 A * 7/1997 Chiu ....................... A61F 5/055 606/54
6,923,779 B1 * 8/2005 Choiniere ............. A61F 13/148 2/311
(Continued)

*Primary Examiner* — Rachael E Bredefeld
*Assistant Examiner* — Seth R. Brown
(74) *Attorney, Agent, or Firm* — Ballard Spahr LLP

(57) ABSTRACT

A trunk exoskeleton is provided including a flexible corset configured to wrap around a user's torso in the lumbar spine region. The flexible corset includes a plurality of vertical pockets formed around its perimeter. A plurality of flexor columns are included, each of which positioned in one of the plurality of vertical pockets. The flexor columns generate a flexor righting torque when bent from a vertical orientation. The multiple flexor righting torques from each of the plurality of flexor columns combine to generate a combined flexor righting torque. The combined flexor righting torque comprises a portion of a user trunk torque when the user's torso is angled from vertical.

17 Claims, 11 Drawing Sheets

(51) Int. Cl.
*A61F 5/01* (2006.01)
*A61N 1/04* (2006.01)
*A61N 1/36* (2006.01)

(52) U.S. Cl.
CPC ................. *A61F 2005/0179* (2013.01); *A61H 2201/5061* (2013.01); *A61N 1/0452* (2013.01); *A61N 1/0484* (2013.01); *A61N 1/36003* (2013.01); *A61N 1/3603* (2017.08)

(58) Field of Classification Search
CPC ............ A41D 13/0012; A41D 13/0015; A41D 13/0525; A41D 13/0531
USPC ............................................................. 602/19
See application file for complete search history.

(56) References Cited

U.S. PATENT DOCUMENTS

| | | | | |
|---|---|---|---|---|
| RE46,069 | E * | 7/2016 | GibsonHorn | A63B 21/4005 |
| 2008/0294081 | A1 * | 11/2008 | Moulin | A61F 5/028<br>602/19 |
| 2010/0268137 | A1 * | 10/2010 | Bachmann | A61F 5/0102<br>602/16 |
| 2014/0180186 | A1 * | 6/2014 | Hyde | A61B 5/1116<br>602/19 |
| 2016/0250062 | A1 * | 9/2016 | Radaelli | A61F 5/028<br>602/16 |
| 2017/0143529 | A1 * | 5/2017 | Ito | A61F 5/05825 |
| 2017/0197078 | A1 * | 7/2017 | Forrest | A61H 3/008 |
| 2017/0354530 | A1 * | 12/2017 | Shagdar | A41D 31/18 |
| 2019/0038484 | A1 * | 2/2019 | Triolo | A61N 1/36003 |
| 2019/0183668 | A1 * | 6/2019 | Thompson | A61F 5/26 |

* cited by examiner

TRUNK EXOSKELETON

CROSS REFERENCE TO RELATED APPLICATION

This application is based upon and claims priority to U.S. Provisional Application No. 63/271,917 filed on Oct. 26, 2021, which is hereby incorporated by reference in its entirety.

FIELD OF THE INVENTION

This invention relates to medical support and treatment devices for individuals paralyzed by spinal cord injury or loss of functional control in the trunk region of the body.

BACKGROUND

Spinal cord injury (SCI) effects nearly 294,000 individuals in the United States and often leads to paralysis severely limiting the ability to perform activities of daily living and reducing quality of life. Specifically, injuries to the spinal cord between the head and the tenth thoracic vertebra (T10) can result paralysis of the lumbar spine often preventing control of seated balance and resulting in a loss of functional abilities and independence. Therefore, regaining trunk stability is reported as the third highest priority for both individuals with paraplegia and tetraplegia outweighing their desire to walk again. Improving dynamic trunk movements for the SCI population would address their concern for trunk stability by increasing their functional capabilities and independence.

Current solutions center around constraining the trunk. An impaired trunk naturally causes a posteriorly titled pelvis increasing anterior stability at the cost of increased risk secondary complications including: spinal deformities, increased spasticity, pressure sore development, neck and shoulder pain, and decreased respiratory function. Lateral stability is obtained through straps and pads often attached to the wheelchair. Even with these tactics, they often have one arm hooked behind their wheelchair or placed in their lap to reach objects and maintain balance. This essentially prevents bilateral hand use outside of a small stable upright region, limiting the available workspace. Additionally, these strategies do little in the presence of potentially destabilizing perturbations commonly experienced while driving a motor vehicle, propelling a manual or powered wheelchair, or performing activities of daily living.

Functional neuromuscular stimulation (FNS) has been shown to improve trunk stability by improving pelvic tilt and bimanual reaching and maintain upright seated posture in the presence of external perturbation. Even large dynamic movements, such as returning to upright from a flexed position, have been achieved with FNS. However, prolonged dynamic movements, like leaning, have yet to be demonstrated partially due to the rapid onset of fatigue and neuroprostheses are unable to leverage the entire strength of the trunk musculature, instead recruiting only a subset of available muscle groups. Additionally, stimulated contractions of paralyzed muscles are estimated to produce 35% less torque than able-body muscles.

It would therefore be desirable to reduce the necessary muscle torque to obtain different trunk postures by mimicking a flexion relaxation phenomenon of the intact spine. The flexion relaxation phenomenon occurs when the trunk is maximally flexed, the extensor muscles then become inactive as the passive properties of the trunk fully supply the required torque to maintain this position. If this phenomenon could be extended to a larger range of trunk positions, the required output of the trunk muscles to maintain a posture would be drastically reduced thereby reducing the impact of fatigue and limited muscle recruitment. It would therefore be desirable to have a device that could expand the range of this phenomena to maximize the effect of FNS on the trunk allowing prolonged dynamics movements.

In addition, it would be desirable to obtain different trunk postures by mimicking the flexion relaxation phenomenon of the intact spine utilizing a purely mechanical structure without the implementation of FNS. This may reduce the complexity and potential cost of implementation while providing an increased availability to individuals.

SUMMARY OF THE INVENTION

An example trunk exoskeleton for use on the lumbar spine region of a user according to the disclosure is comprised of a flexible corset and a plurality of flexor columns. The flexible corset is configured to wrap around the user's torso in the lumbar spine region. The flexible corset comprises a plurality of vertical pockets formed around its perimeter. The plurality of flexor columns are positioned within the plurality of vertical pockets. Each of the plurality of flexor columns has a column top and a column bottom. Each of the plurality of flexor columns generates a flexor righting torque when bent from a vertical orientation. The flexor righting torques from the plurality of flexor columns generate a combined flexor righting torque. The combined flexor righting torque comprises a portion of a user trunk torque when the user's torso is angled from vertical.

In an example embodiment, the trunk exoskeleton further comprises a functional neuromuscular stimulation assembly mounted to an interior of the flexible corset. The functional neuromuscular stimulation assembly comprises a stimulation controller, at least one sensor, and one or more electrodes in communication with the stimulation controller. The one or more electrodes is in direct contact with the user's skin when the flexible corset is wrapped around the user's torso. The one or more electrodes provide electrical stimulation to the user's muscles to generate stimulated trunk torque. The combined flexor righting torque and the stimulated trunk torque combined comprise at least 75% of the user trunk torque when the user's torso is angled from vertical.

In an example embodiment, each of the plurality of flexor columns comprises a semi-elastic rod.

In an example embodiment, the plurality of flexor columns are removable from the pocket such that the user can adjust the number of semi-elastic rods.

In an example embodiment, each of the plurality of flexor columns comprises a plurality of rigid cylindrical rings and a plurality of spring element positioned between each of the plurality of rigid cylindrical rings. Each of the plurality of rigid cylindrical rings includes a lower spring engagement surface and an upper spring engagement surface. The plurality of spring elements is positioned between each of the plurality of rigid cylindrical rings such that each of the plurality of spring elements engages an upper spring engagement surface of one of the plurality of rigid cylindrical rings and the lower spring engagement surface of a neighboring one of the plurality of rigid cylindrical rings.

In an example embodiment, each of the plurality of rigid cylindrical rings includes a rotation limiting protrusion adjacent the lower spring engagement surface. The rotation limiting protrusion is positioned within the upper spring engagement surface of a neighboring one of the plurality of rigid cylindrical rings.

In an example embodiment, the rotation limiting protrusions limit the flexor columns from bending more than 60 degrees measured from the column bottom to the column top.

In an example embodiment, each of the flexor columns is limited from bending more than 60 degrees measured from the column bottom to the column top.

In an example embodiment, the combined flexor righting torque is adjusted by modifying the number of the semi-elastic rods.

In an example embodiment, the combined flexor righting torque is adjusted by modifying the cross-section of the semi-elastic rods.

In an example embodiment, the trunk exoskeleton further comprises a base mount positioned within a lower region of the flexible corset. The base mount comprising a plurality of base rigid links rotationally engaged to each other. Each of the plurality of base rigid links includes a base retention slot to house one of the plurality of flexor columns.

In an example embodiment, the trunk exoskeleton further comprises a top mount positioned within an upper region of the flexible corset. The top mount comprises a plurality of top rigid links rotationally engaged to each other. Each of the plurality of top rigid links includes a top retention slot to house one of the plurality of flexor columns.

In an example embodiment, the trunk exoskeleton further comprises a securing mount in communication with the base mount for securing the flexible corset relative to the user.

In an example embodiment, the securing mount is a belt engagement loop.

In an example embodiment, the trunk exoskeleton further comprises one or more alignment markers mounted on the flexible corset to allow the user to align the one or more electrodes.

In an example embodiment, the one or more alignment markers are positioned to align with a user's navel or axilla.

In an example embodiment, the trunk exoskeleton further comprises an inertial measurement unit sensor mounted on the flexible corset in communication with the stimulation controller.

In an example embodiment, the trunk exoskeleton further comprises a functional neuromuscular stimulation assembly comprising a stimulation controller, one or more communication regional interfaces mounted to an interior of the flexible corset and in communication with the stimulation controller, and one or more removable electrodes attachable directly to the user's skin. When the flexible corset is wrapped around the user's torso the one or more removable electrodes are placed in communication with the one or more communication regional interfaces. The one or more electrodes provide electrical stimulation to the user's muscles to generate stimulated trunk torque in response to signals sent from the one or more communication regional interfaces as directed by the stimulation controller. The combined flexor righting torque and the stimulated trunk torque combined comprise at least 75% of the user trunk torque when the user's torso is angled between from vertical.

The disclosure further encompasses a trunk exoskeleton for use on the lumbar spine region of a user comprising a flexible corset, a plurality of flexor columns, and a functional neuromuscular stimulation assembly. The flexible corset is configured to wrap around the user's torso in the lumbar spine region. The plurality of flexor columns is positioned vertically within the flexible corset. Each of the plurality of flexor columns has a column top and a column bottom. Each of the plurality of flexor columns generates a flexor righting torque when bent from a vertical orientation. The flexor righting torques from the plurality of flexor columns generate a combined flexor righting torque. The functional neuromuscular stimulation assembly comprises a stimulation controller and one or more electrodes in communication with the stimulation controller. The one or more electrodes is in direct contact with the user's skin when the flexible corset is wrapped around the user's torso. The one or more electrodes provide electrical stimulation to the user's muscles to generate a stimulated trunk torque. The combined flexor righting torque and the stimulated trunk torque combined replace a portion of a user's trunk torque.

The disclosure further encompasses a method of improving the range of motion of a user. The method comprises wrapping a flexible corset around the user's torso in the lumbar spine region, attaching a functional neuromuscular stimulation assembly to the user, and providing electrical stimulation to the user's muscles to generate a stimulated trunk torque. The flexible corset includes a plurality of flexor columns positioned vertically. Each of the plurality of flexor columns has a column top and a column bottom. Each of the plurality of flexor columns generates a flexor righting torque when bent from a vertical orientation. The flexor righting torques from the plurality of flexor columns generate a combined flexor righting torque. The functional neuromuscular stimulation assembly includes a stimulation controller and one or more electrodes in direct contact with the user's skin. The combined flexor righting torque and the stimulated trunk torque combine to replace a portion of a user's trunk torque.

DETAILED DESCRIPTION

The present disclosure can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

Figure 1:
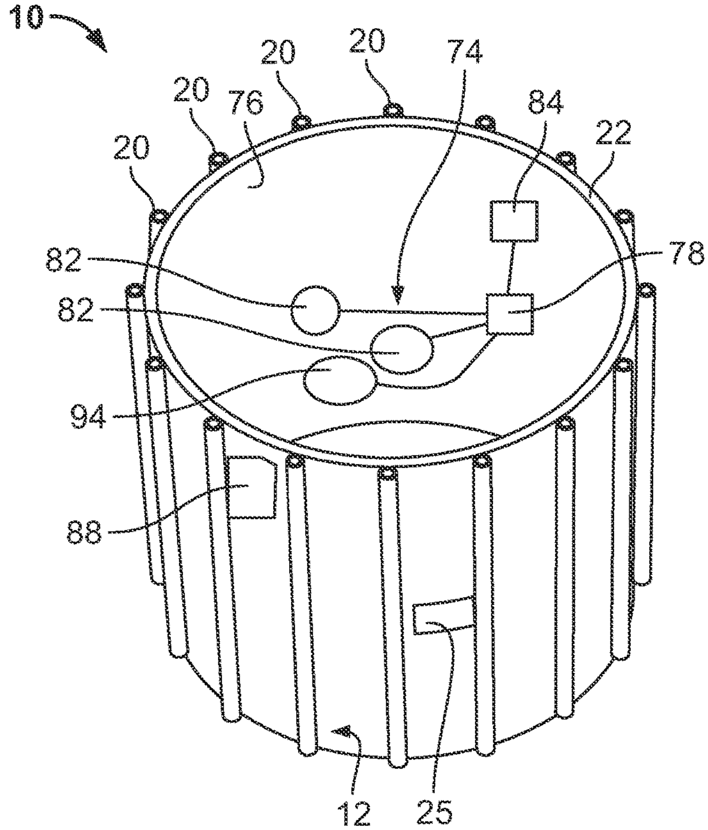
FIG. 1 is an isometric view of a trunk exoskeleton according to the disclosure.
Figure 2:
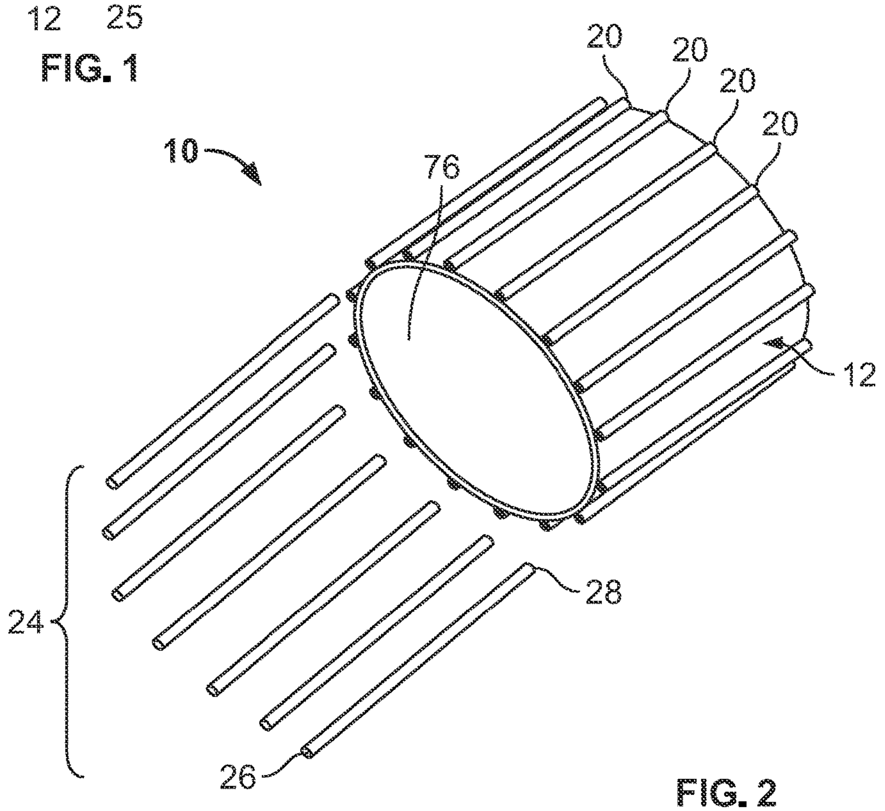
FIG. 2 is an isometric view of the trunk exoskeleton shown in FIG. 1, the figure showing the flexor columns removed from the vertical pockets.
Figure 3:
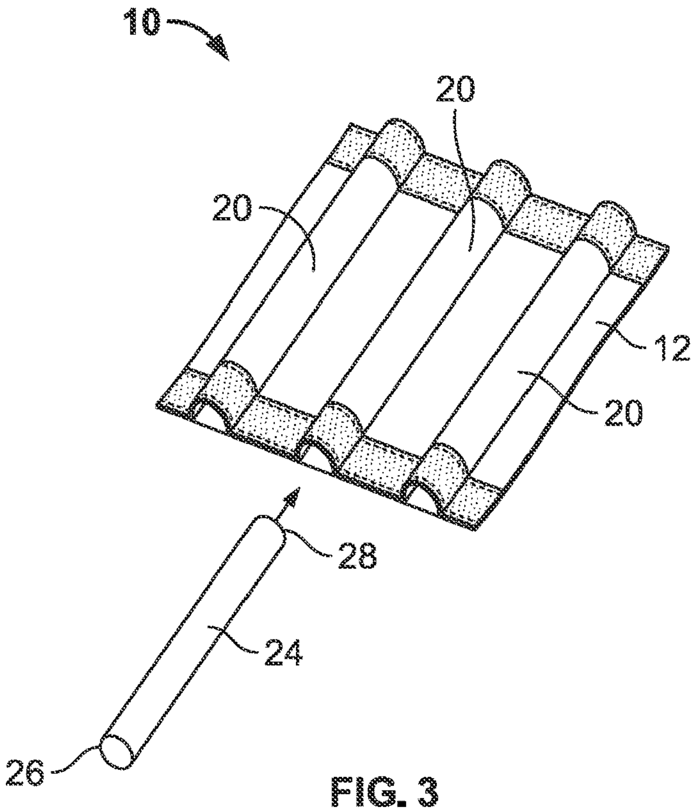
FIG. 3 is a plan view of the trunk exoskeleton shown in FIG. 1, the figure showing the flexible corset lying flat.

FIGS. 1-3 show an example of a trunk exoskeleton 10 according to the disclosure. The trunk exoskeleton 10 includes a flexible corset 12 that is wrapped around the torso 14 of a user 16 in the lumbar spine region 18 (see FIG. 4). The flexible corset 12 in one example is made of a flexible fabric or material such as neoprene. The flexible corset 12 can include a plurality of vertical pockets 20 formed around the flexible corset perimeter 22. These may be formed onto the flexible corset 12 or may be sewn in. The trunk exoskeleton 10 also includes a plurality of flexor columns 24 (see FIGS. 2 and 3), each having a column top 26 and a column bottom 28. Each of plurality of flexor columns 24 are positioned in one of the plurality of vertical pockets 20. The flexible corset 12 may further include a corset securing element 25 such as a Velcro latch to secure the flexible corset 12 once it has been wrapped around the user 16. As shown in FIG. 5, alternatively or in addition, the flexible corset 12 may include at least one buckle 27 as the corset securing element 25 to secure the flexible corset 12 around the user 16. In other examples, the corset securing feature 25 may comprise buttons, latches, zippers or synchs.

Figure 6:
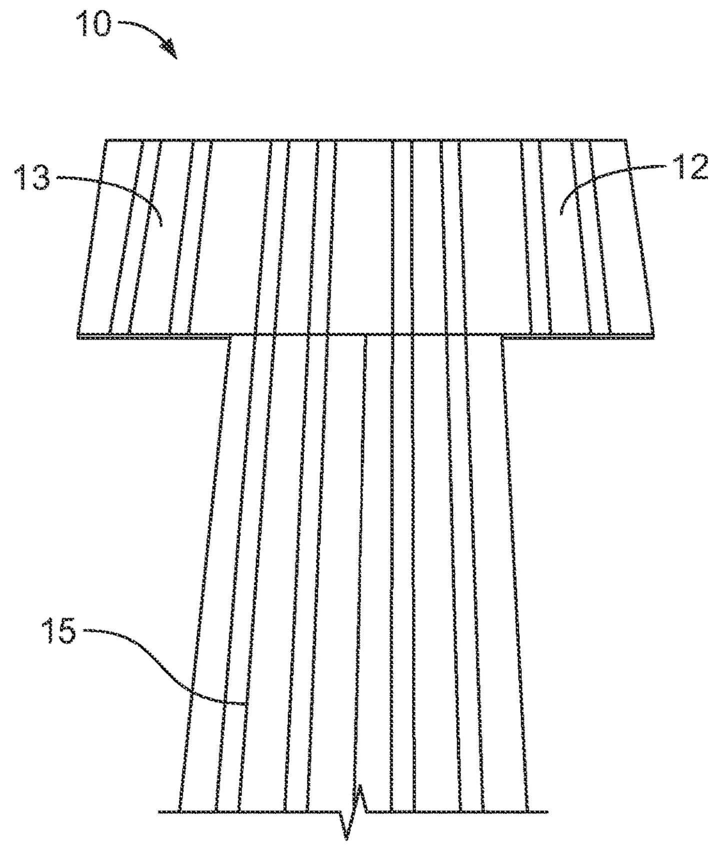
FIG. 6 is a plan view of a T-shaped exoskeleton.
Figure 7:
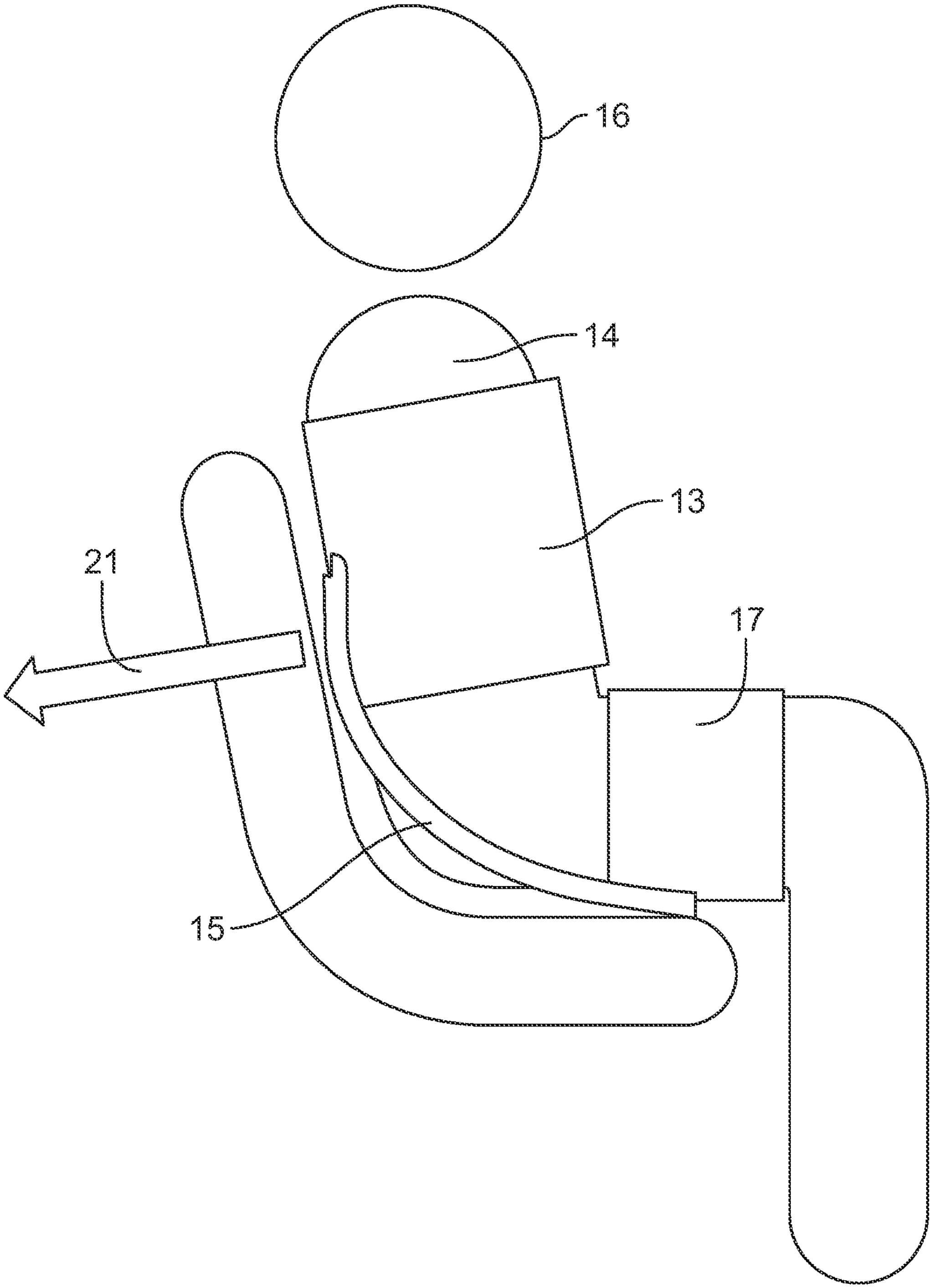
FIG. 7 is an isometric view of the trunk exoskeleton shown in FIG. 6 as applied to a user's torso.

It should be understood that although the flexible corset 12 is illustrated as symmetrical, a variety of shapes are contemplated by this disclosure. In one example, the back of the flexible corset 12 may be higher than the front to prevent "riding up" when the user bends forward. In another example, the bottom of the flexible corset 12 may be angled or recessed to fit over the hips and may be longer in the front or back. In still another example, the flexible corset 12 may be shaped to drape below the pelvis in the front and/or back. In yet another example, the flexible corset 12 may be V-shaped to account for a user having muscles of the upper back that are wider than the waist. As shown in FIG. 6, the flexible corset 12 may be T-shaped including a top section 13 and a bottom section 15. The flexor columns 24 may extend from the top section 13 to the bottom section 15. As shown in FIG. 7, the top section 13 may be configured to wrap around the torso 14 of a user 16. The bottom section 15 and flexor columns 24 may wrap underneath the user's pelvis. In one example, the bottom section 15 may be secured at the thigh by a third section 17. The flexor columns 24 wrapping from the user's 16 torso 14 to thigh may provide a restorative force 21 in the form of a flexor righting torque 36 as described herein with a fulcrum point at the user's pelvis. The flexible corset 12 and corresponding flexor columns 12 may have a customizable shape to fit the needs and physique of the user 16.

Figure 8:
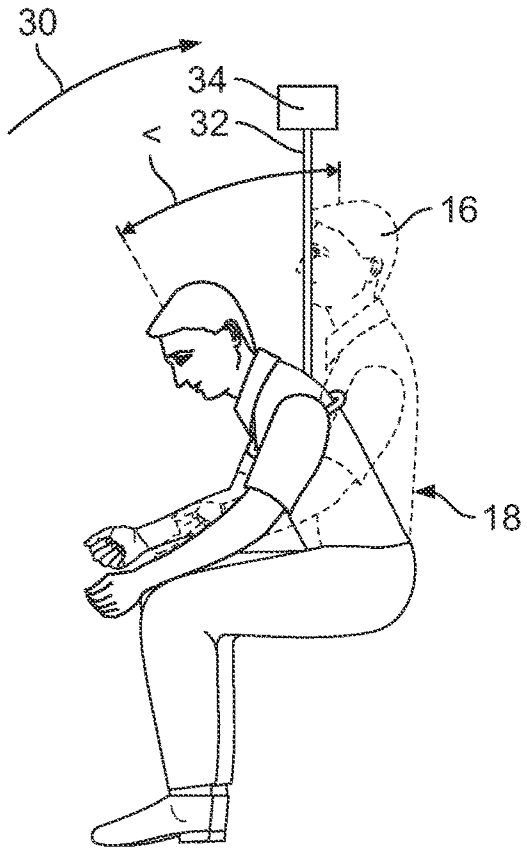
FIG. 8 is a side view illustration of a user illustrating a range of motion along with one example of measuring user trunk torque.

The required user trunk torque 30 is the torque required by a user's various muscle groups to maintain a position when the user 16 is angled from vertical in flexion, extension, and lateral bending (see FIG. 8). It can be measured in a variety of fashions. In one example, the user 16 is angled forward and suspended by a rope 32 attached to a load cell 34 to measure the lumbar torque/user trunk torque 30. This procedure may be repeated over a variety of angles and a number of users to develop statistical models to predict the required user trunk torque 30 at any given angle/position. In one example, the user trunk torque 30 for any given position is determined by measurements derived from healthy individuals without back problems.

Figure 9:
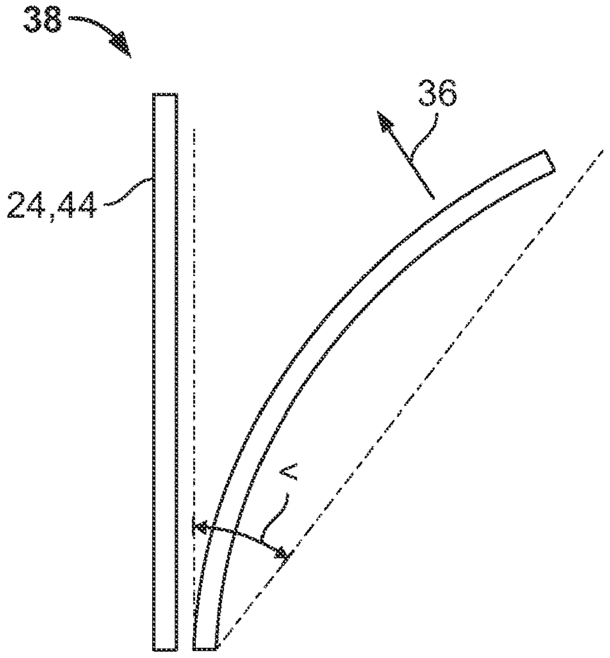
FIG. 9 is an illustration of a flexor column/semi-elastic rod for use in the trunk exoskeleton shown in FIGS. 1-7.
Figure 10:
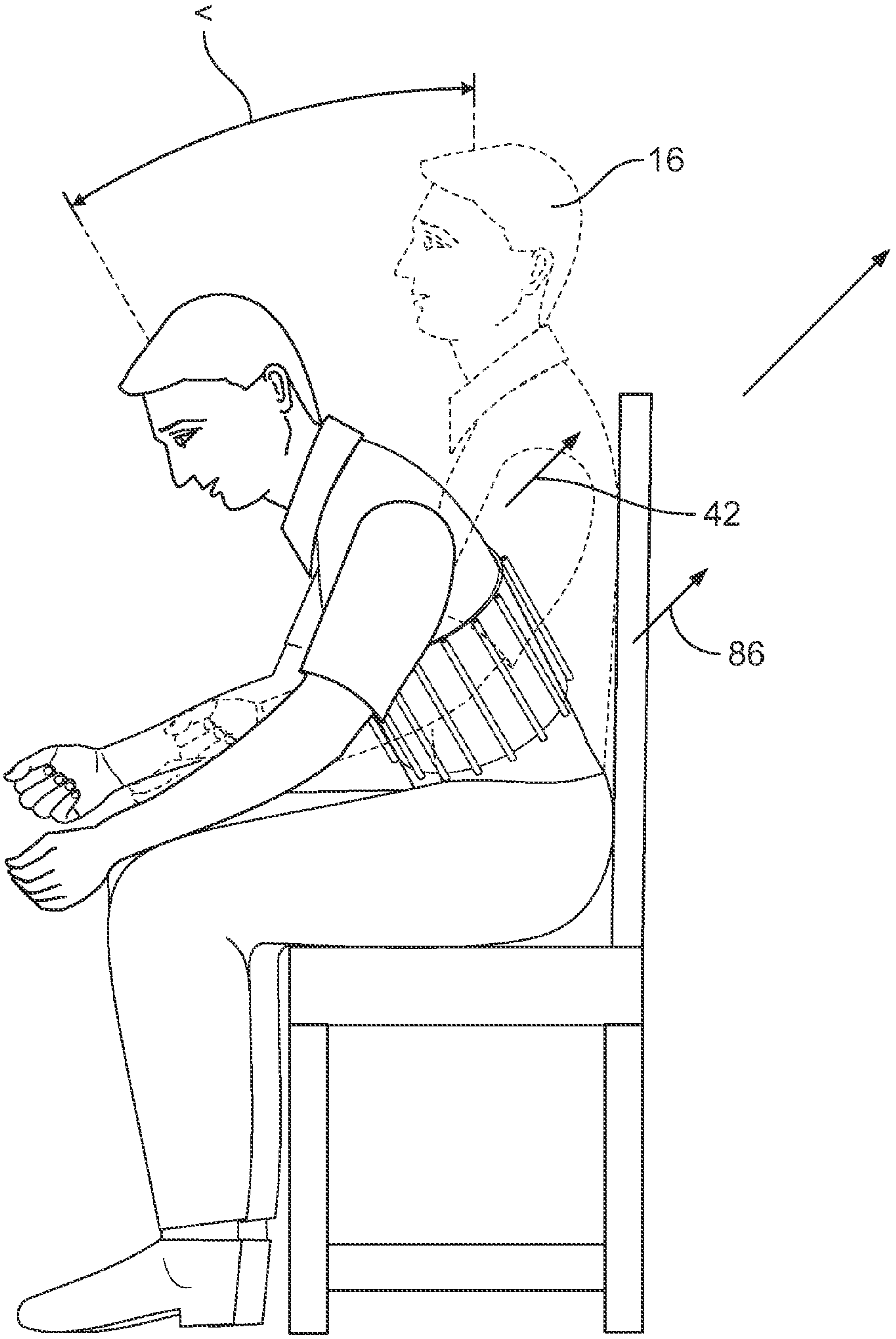
FIG. 10 is a side view illustration of a user wearing the trunk exoskeleton shown in FIGS. 1-3, the illustration showing range of user motion, combined flexor righting torque, and stimulated trunk torque.

Referring now to FIG. 9, each of the plurality of flexor columns 24 generates a flexor righting torque 36 when bent from a vertical orientation 38. The flexor righting torque 36 will increase as the bend angle 40 increases. When a plurality of flexor columns 24 are used, the flexor righting torques 36 combine to generate a combined flexor righting torque 42 as shown in FIG. 10. In one example, the combined flexor righting torque 42 comprises at least 90% of the user trunk torque 30 when the user's torso 14 is angled from vertical. In another example, the combined flexor righting torque 42 comprises at least 75% of the user trunk torque 30 when the user's torso 14 is angled from vertical. In other examples, the combined flexor righting torque 42 may comprise any percentage of the user trunk torque 30 when the user's torso 14 is angled from vertical to accommodate optimal performance for individual users.

Figure 4:
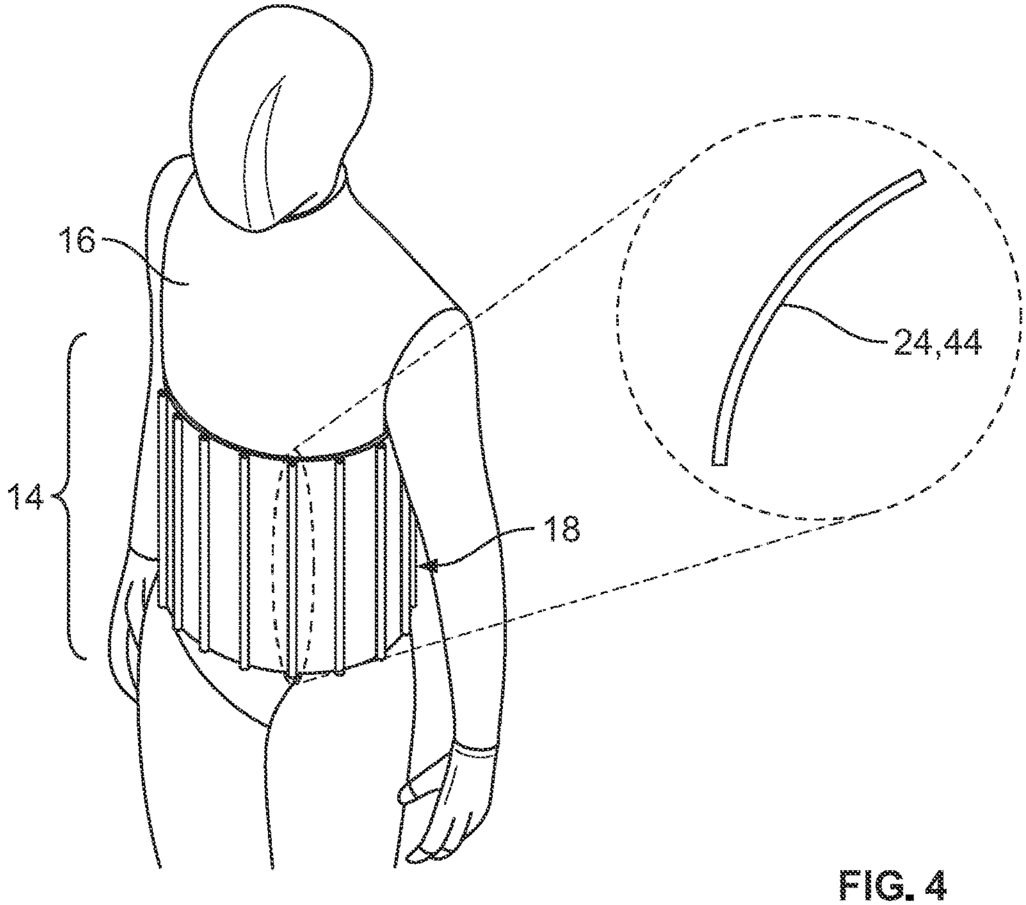
FIG. 4 is an isometric view of the trunk exoskeleton shown in FIG. 1 as applied to a user's torso.
Figure 5:
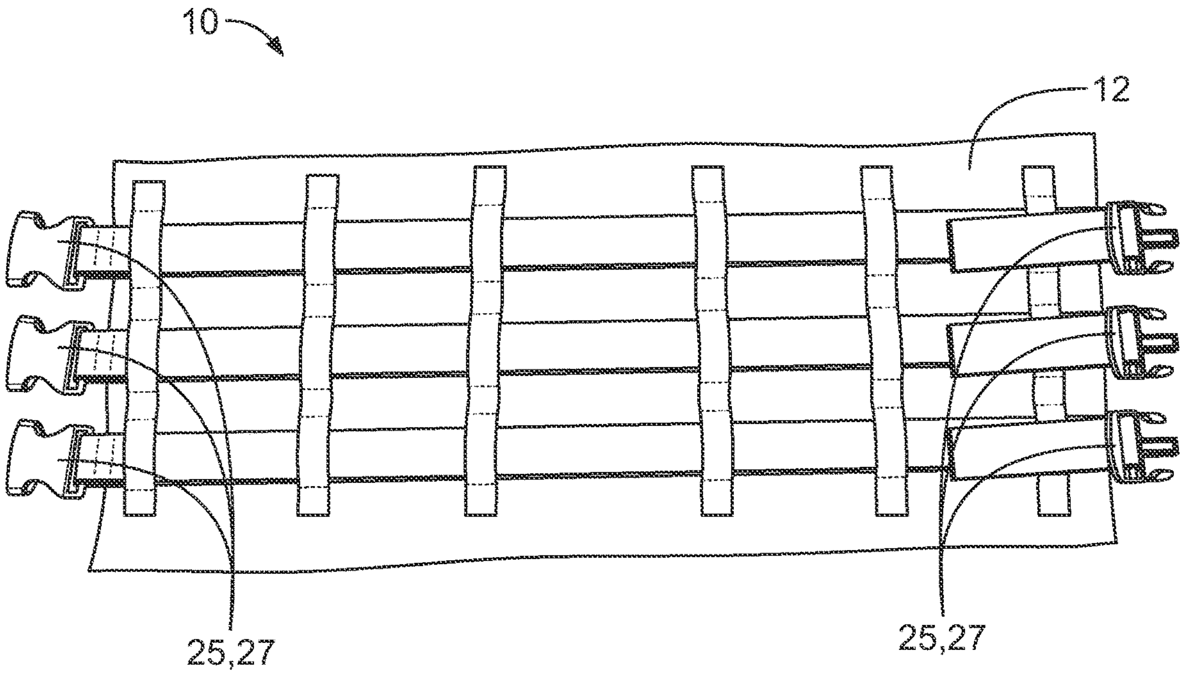
FIG. 5 is a plan view of the trunk exoskeleton shown in FIG. 1 showing an exemplary embodiment of the corset securing elements.

In one example, shown in FIG. 4 and FIG. 9, each of the plurality of flexor columns 24 may comprise a semi-elastic rod 44. It is contemplated that the flexor righting torque 36 and the resultant combined flexor righting torque 42 may be controlled in a variety of fashions. In one example, the material property of the semi-elastic rod 44 may be chosen to produce a desired flexor righting torque 36. In another example, the cross-section of the semi-elastic rod maybe increased or decreased to achieve a desired flexor righting torque 36. In still another example the cross-section may be non-symmetrical such as an oval or a beam to allow for the flexor righting torque 36 to differ depending on the direction of the user's 16 bending. This can allow each of the semi-elastic rods 44 to provide a varied amount of flexor righting torque 42 depending on the direction the user 16 bends. For example, this can allow the semi-elastic rods 44 on a user's back to contribute more or less to the combined flexor righting torque 42 when the user 16 bends to the side and the semi-elastic rods 44 on a user's side to contribute more or less to the combined flexor righting torque 42 when the user 16 bends forward. In still another example, the number of semi-elastic rods 44 can be increased or decreased (overall or within each vertical pocket 20) to control the combined flexor righting torque 42. In at least one example, the semi-elastic rods 44 can be removed and inserted by the user 16. This allows the user 16 to adjust the type or number of semi-elastic rods 44 to their own preference, to adjust for a particular task or position, or even to accommodate their changing needs over time. In another example, the length of the semi-elastic rods 44 may be selected to adjust the combined flexor righting torque 42. For example, the semi-elastic rods 44 may have a length to accommodate only the user's trunk 14. Alternatively, at least some of the semi-elastic rods 44 may have a length to wrap from the user's trunk 14 to under the user's pelvis and/or thighs as shown in FIG. 7. The amount, type, length, and number of rods can be easily tuned to closely match the target lumbar torque/user trunk torque 30 and to overshoot or undershoot to adjust for different bodyweights. In one example, the combined flexor righting torque 42 is chosen from a selection of semi-elastic rods 44 to be at least 90% of the user trunk torque 30. In another example, the combined flexor righting torque 42 is chosen from a selection of semi-elastic rods 44 to be at least 75% of the user trunk torque 30.

Figure 11:
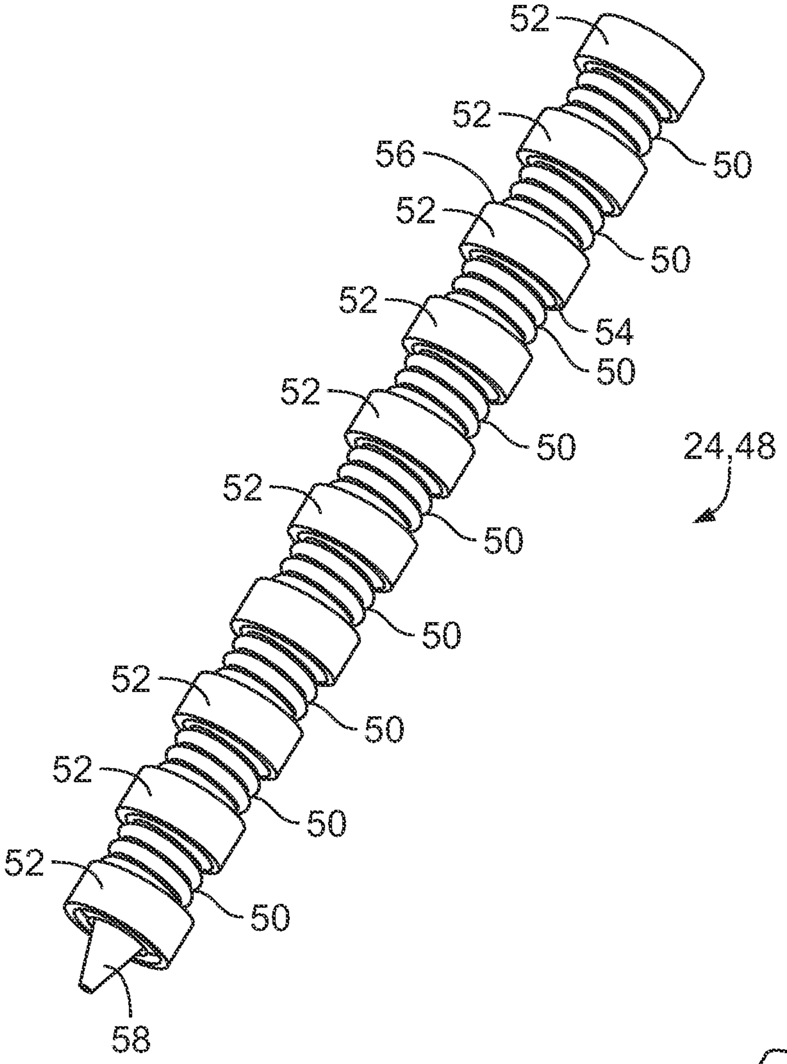
FIG. 11 is an example of a flexor column comprised of a spinal spring assembly.
Figure 12:
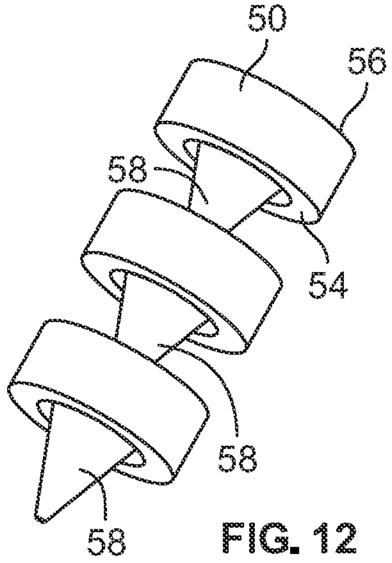
FIG. 12 is a detail of the spinal spring assembly shown in FIG. 11, the detail eliminating the spring elements to allow a view of the rigid cylindrical rings.

In an example shown in FIG. 11, each of the plurality of flexor columns 24 may comprise a spinal spring assembly 48. The spinal spring assembly 48 includes a plurality of spring elements 50 positioned between a plurality of rigid cylindrical rings 52 in series. Each of the plurality of rigid cylindrical rings 52 has a lower spring engagement surface 54 and an upper spring engagement surface 56. In one example, each of the plurality of rigid spring elements 50 may further include a rotation limiting protrusion 58 positioned adjacent the lower spring engagement surface 54 (see FIG. 12—spring elements 50 removed for visualization). The rotation limiting protrusions 58 protrude into a neighboring rigid cylindrical ring 52 adjacent the upper spring engagement surface 56 to limit rotation. In one example this limits the rotation of the spinal spring assembly 48 from bending more than 60 degrees as measured from column bottom 28 to column top 26. In other examples, the limitation of rotation can be set to other angles. In the example shown, the rotation limiting protrusion 58 comprises a conical shaped protrusion. However a variety or rotation limiting protrusions 58 are contemplated. In one example, the number of spring elements 50 and corresponding rigid cylindrical rings 52 may be adjusted to achieve the desired combined flexor righting torque 42. In other examples, the tension of the spring elements 50 may be modified to achieve the desired combined flexor righting torque 42.

Figure 13:
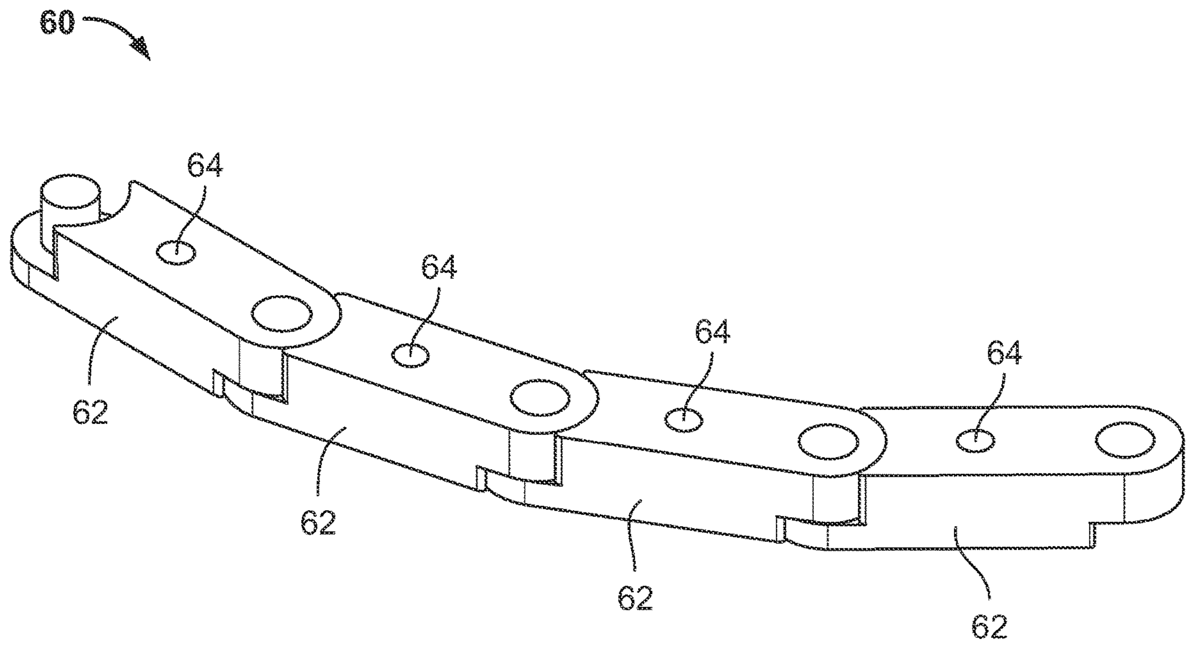
FIG. 13 is an isometric view of a base mount for use with the trunk exoskeleton shown in FIG. 1.
Figure 14:
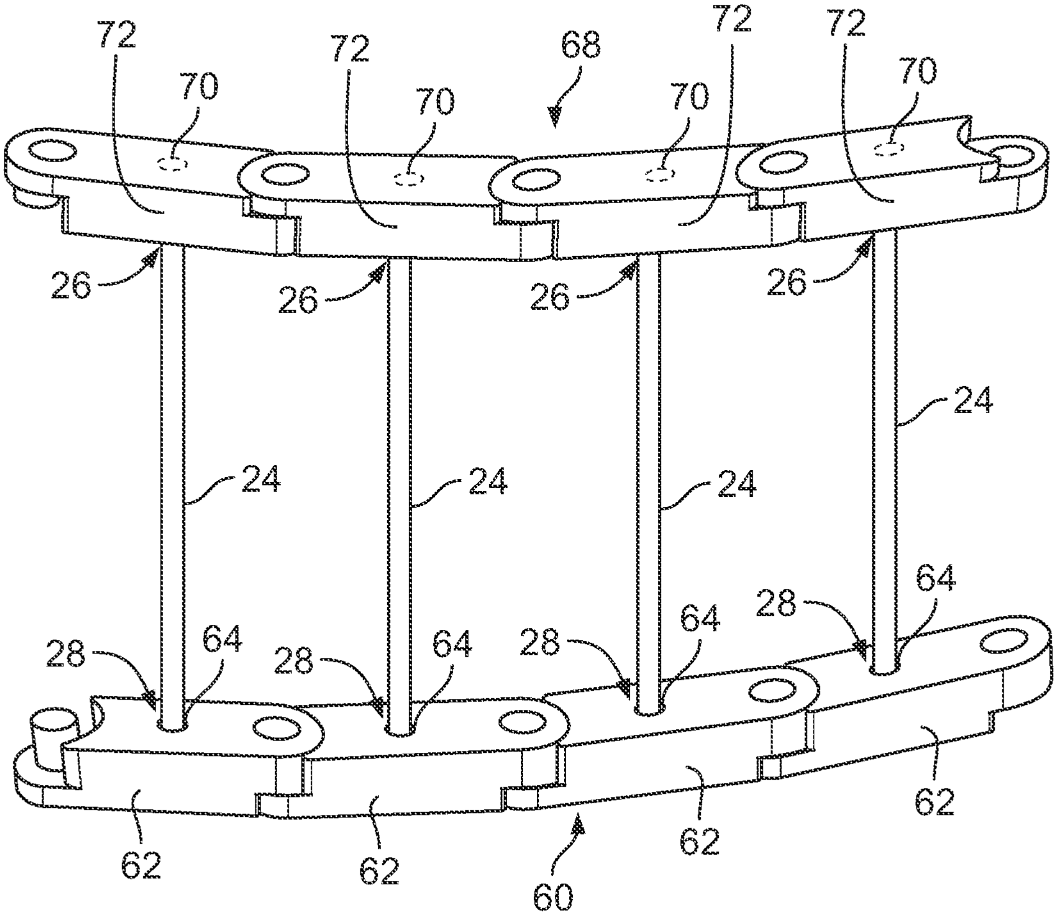
FIG. 14 is an isometric view of the base mount shown in FIG. 13, the base mount shown in combination with a top mount.

Referring now to FIGS. 13 and 14, the trunk exoskeleton 10 may further include a base mount 60 positioned within a lower region of the flexible corset 12. The base mount 60 is utilized to restrain the column bottoms 28 of the plurality of flexor columns 24. The base mount 60 is comprised of a plurality of base rigid links 62 rotationally engaged to one another. Each of the base rigid links 62 contains one or more base retention slots 64 configured to engage and house the column bottom 28 of one of the plurality of flexor columns 24. The base mount 60 may further include a securing mount for securing the base relative to the user 16. In one example, the securing mount may comprise a belt engagement loop to engage a user's belt (not shown). In another example, the securing mount may comprise a connection to the user's wheelchair. In still another example, the securing mount may comprise a connection to a plate positioned under the user 16 while seated. In another example, the trunk exoskeleton 10 may further include a top mount 68 positioned in an upper region of the flexible corset 12. The top mount 68 secures the column top 26 of each of the plurality of flexor columns 24. In one example, the top mount 68 is identical to the bottom mount 60 and includes a plurality of top rigid links 72 rotationally engaged to one another. Each of the plurality of top rigid links 72 includes one or more top retention slots 70 configured to engage the column top 26 of one of the plurality of flexor columns 24.

Although the trunk exoskeleton 10 may be utilized alone as described above, in other examples it may further include a functional neuromuscular stimulation (FNS) assembly 74 mounted to or within the flexible corset 12 (see FIG. 1). In one example, the FNS assembly 74 is mounted on an interior 76 of the flexible corset 12. The FNS assembly 74 includes a stimulation controller 78. The stimulation controller 78 may be mounted on either the interior 76 or exterior 80 of the flexible corset 12. The stimulation controller 78 is in communication with one or more electrodes 82. In one example, the FNS assembly 74 may also include one or more sensors 84 in communication with the stimulation controller 78 to provide feedback. The one or more electrodes 82 are positioned on the interior 76 of the flexible corset 12 is positions to make direct contact with the user's skin when the flexible corset 12 is positioned on the user's torso 14. The simulation controller 78 sends signals to the one or more electrodes 82 to provide electrical stimulation to the motor nerves activating the user's muscles. This, in turn, generates a stimulated trunk torque 86 within the user's torso 14. The FNS assembly 74 may further include one or more inertial measurement unit (IMU) sensors 88 attached to the flexible corset 12 and in communication with the stimulation controller 78. In one example the IMU 88 comprises a 9-axis IMU. The IMU is utilized by the stimulation controller 78 to determine the direction and angle of a user 16. This, in turn, allows the stimulation controller 78 to send an appropriate level of stimulation to the user's muscles via the electrodes 82 to generate a stimulated trunk torque 86 specific to the user's positioning. The stimulated trunk user torque 86 combines with the combined flexor righting torque 42 to generate at least 75%-90% of the user trunk torque 30 (see FIG. 7). In one example, the flexible corset 12 generates the majority of the user trunk torque 30 while the FNS assembly 74 is used to fine tune the percentage of user trunk torque 30. Although in the example cited above, the stimulated trunk torque 86 combines with the combined flexor righting torque 42 to generate at least 75%-90% of the user trunk torque 30, in other examples the percentage could be higher as long as it does not overly restrict user trunk movement.

Figure 15:
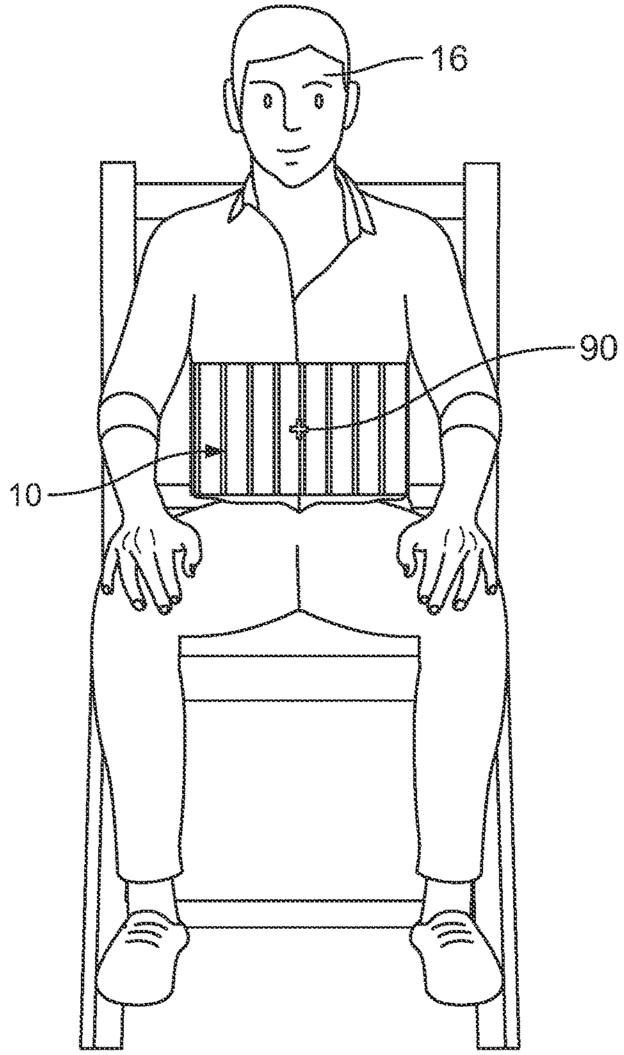
FIG. 15 is a front view of a user wearing the trunk exoskeleton shown in FIG. 1, this example showing a movable alignment marker positioned on the front of the flexible corset.
Figure 16:
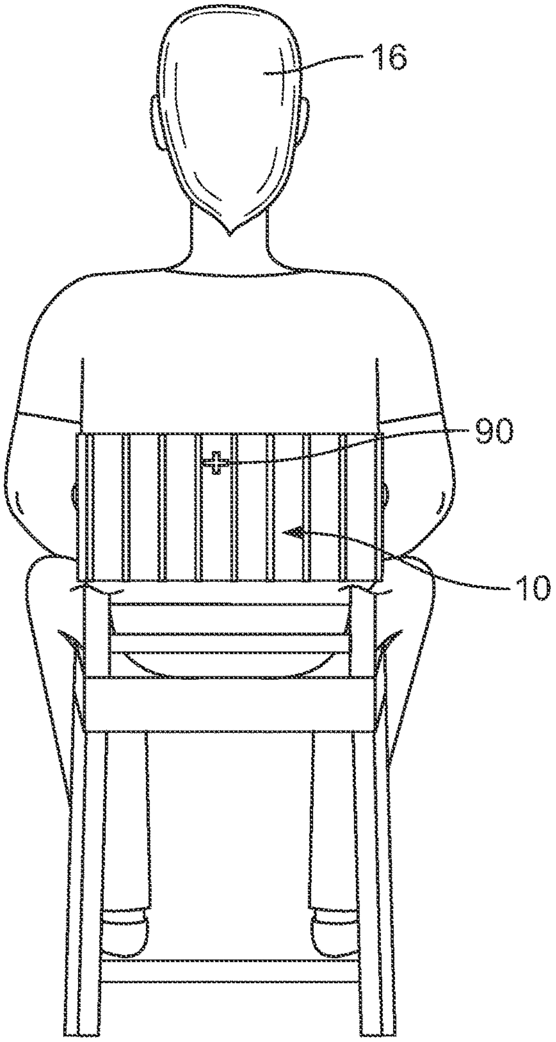
FIG. 16 is a rear view of the user shown in FIG. 15, this example showing a movable alignment marker positioned on the back of the flexible corset.
Figure 17:
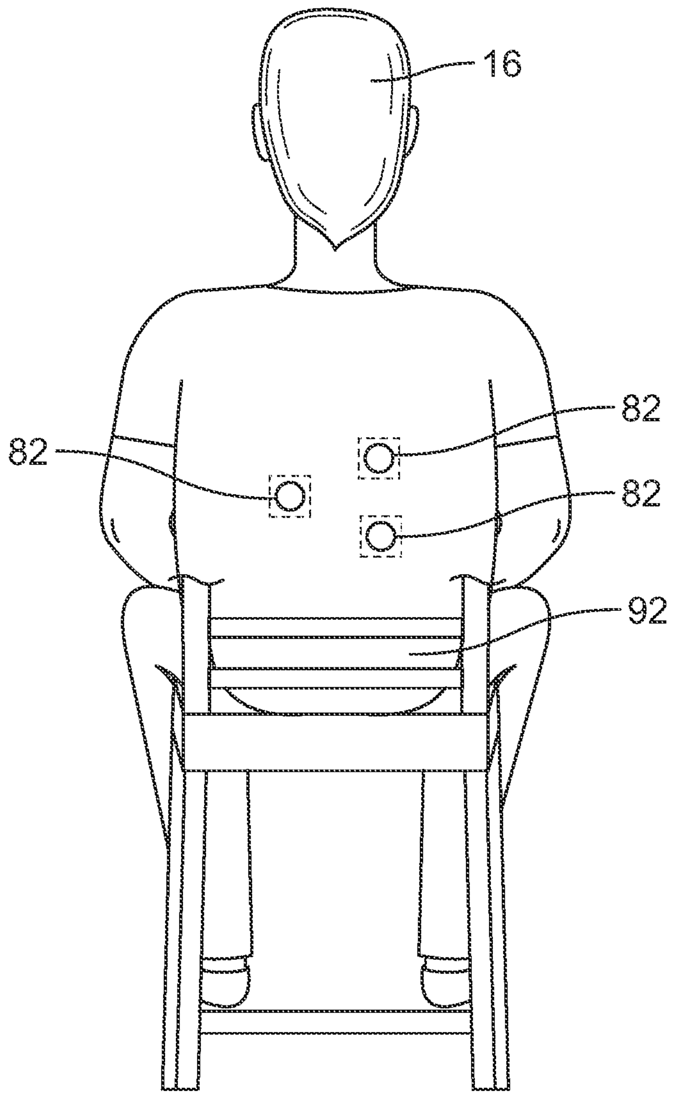
FIG. 17 is a rear view of a user in the sitting position, this example illustrating removable electrodes placed directly on the user's skin.

The trunk exoskeleton 10 may include one or more movable alignment markers 90 positioned on the flexible corset 12 (see FIGS. 15-16) to assist in aligning the electrodes 82 with the correct muscle groupings on the user's torso 14. In one embodiment these alignment markers 90 are mapped to landmarks on the torso such as the axilla (space between shoulders) and umbilicus (naval). By aligning the alignment markers 90 to the body landmarks, the proper positioning of the electrodes 82 is quickly and easily achieved. In one example, an alignment marker 90 can comprise a hole in the flexible corset 12 at the user's umbilicus (naval) such that proper orientation can be achieved by visually inspecting the naval through the hold. In another example, the electrodes 82 are removable and/or temporary electrodes attached directly to the user's skin 92 as seen in FIG. 17. In this example, the stimulation controller 78 is in communication with one or more communication regional interfaces 94 mounted on the interior 76 of the flexible corset 12 (see FIG. 1). The communication regional interfaces 94 are significantly larger in size than the electrodes 82. The communication regional interfaces 94 send electrical impulses to electrodes 82, in response to signals received from the stimulation controller 78, that they make physical contact with similar in nature to wireless charging. In this example, the electrodes 82 may be placed in precise locations while the flexible corset 12 need only be generally aligned. This example also allows the flexible corset 12 to permit small levels of shifting without disrupting the positioning or functionality of the electrodes 82.

All of the embodiments of the claimed invention described herein are provided expressly by way of example only. Innumerable variations and modifications may be made to the example embodiments described herein without departing from the concept of this disclosure. Additionally, the scope of this disclosure is intended to encompass any and all modifications and combinations of all elements, features, and aspects described in the specification and claims, and shown in the drawings. Any and all such modifications and combinations are intended to be within the scope of this disclosure.

What is claimed is:

1. A trunk exoskeleton for use on the lumbar spine region of a user, the trunk exoskeleton comprising:

a flexible corset configured to wrap around the user's torso in the lumbar spine region, the flexible corset comprising a plurality of vertical pockets formed around its perimeter; and a plurality of flexor columns positioned within the plurality of vertical pockets, each of the plurality of flexor columns having a column top and a column bottom, each of the plurality of flexor columns generating a flexor righting torque when bent from a vertical orientation, the flexor righting torques from the plurality of flexor columns generating a combined flexor righting torque;

wherein the combined flexor righting torque comprises a portion of a user trunk torque when the user's torso is angled from vertical, and wherein each of the plurality of flexor columns comprises:

a plurality of rigid cylindrical rings, each of the plurality of rigid cylindrical rings including a lower spring engagement surface and an upper spring engagement surface; and a plurality of spring elements positioned between each of the plurality of rigid cylindrical rings such that each of the plurality of spring elements engages the upper spring engagement surface of one of the plurality of rigid cylindrical rings and the lower spring engagement surface of a neighboring one of the plurality of rigid cylindrical rings.

2. The trunk exoskeleton according to claim 1, further comprising:

a functional neuromuscular stimulation assembly mounted to an interior of the flexible corset, the functional neuromuscular stimulation assembly comprising:

a stimulation controller;

at least one sensor; and one or more electrodes in communication with the stimulation controller, the one or more electrodes in direct contact with the user's skin when the flexible corset is wrapped around the user's torso;

wherein the one or more electrodes are configured to provide electrical stimulation to the user's muscles to generate stimulated trunk torque;

wherein the combined flexor righting torque and the stimulated trunk torque combined comprise at least 75% of the user trunk torque when the user's torso is angled from vertical.

3. The trunk exoskeleton according to claim 1, wherein each of the plurality of flexor columns comprises a semi-elastic rod.

4. The trunk exoskeleton according to claim 1, wherein the plurality of flexor columns are removable from the pocket such that the user can adjust the number of semi-elastic rods.

5. The trunk exoskeleton according to claim 1, wherein each of the plurality of rigid cylindrical rings includes a rotation limiting protrusion adjacent the lower spring engagement surface, the rotation limiting protrusion positioned within the upper spring engagement surface of a neighboring one of the plurality of rigid cylindrical rings.

6. The trunk exoskeleton according to claim 5, wherein the rotation limiting protrusions limit the flexor columns from bending more than 60 degrees measured from the column bottom to the column top.

7. The trunk exoskeleton according to claim 1, wherein each of the flexor columns is limited from bending more than 60 degrees measured from the column bottom to the column top.

8. The trunk exoskeleton according to claim 1, wherein the combined flexor righting torque is adjusted by modifying the number of the semi-elastic rods.

9. The trunk exoskeleton according to claim 1, wherein the combined flexor righting torque is adjusted by modifying the cross-section of the semi-elastic rods.

10. A trunk exoskeleton for use on the lumbar spine region of a user, the trunk exoskeleton comprising:

a flexible corset configured to wrap around the user's torso in the lumbar spine region, the flexible corset comprising a plurality of vertical pockets formed around its perimeter;

a plurality of flexor columns positioned within the plurality of vertical pockets, each of the plurality of flexor columns having a column top and a column bottom, each of the plurality of flexor columns generating a flexor righting torque when bent from a vertical orientation, the flexor righting torques from the plurality of flexor columns generating a combined flexor righting torque; and a base mount positioned within a lower region of the flexible corset, the base mount comprising a plurality of base rigid links rotationally engaged to each other, each of the plurality of base rigid links including a base retention slot to house one of the plurality of flexor columns, wherein the combined flexor righting torque comprises a portion of a user trunk torque when the user's torso is angled from vertical.

11. The trunk exoskeleton according to claim 10, further comprising:

a top mount positioned within an upper region of the flexible corset, the top mount comprising a plurality of top rigid links rotationally engaged to each other, each of the plurality of top rigid links including a top retention slot to house one of the plurality of flexor columns.

12. The trunk exoskeleton according to claim 10, further comprising:

a securing mount in communication with the base mount for securing the flexible corset relative to the user.

13. The trunk exoskeleton according to claim 12, wherein the securing mount is a belt engagement loop.

14. The trunk exoskeleton according to claim 2, further comprising:

one or more alignment markers mounted on the flexible corset to allow the user to align the one or more electrodes.

15. The trunk exoskeleton according to claim 14, wherein the one or more alignment markers are positioned to align with the user's navel or axilla.

16. The trunk exoskeleton according to claim 2, further comprising:

an inertial measurement unit sensor mounted on the flexible corset in communication with the stimulation controller.

17. The trunk exoskeleton according to claim 1, further comprising:

a functional neuromuscular stimulation assembly comprising:

a stimulation controller;

one or more communication regional interfaces mounted to an interior of the flexible corset and in communication with the stimulation controller; and one or more removable electrodes attachable directly to the user's skin, when the flexible corset is wrapped around the user's torso the one or more removable electrodes are placed in communication with the one or more communication regional interfaces;

wherein the one or more electrodes are configured to provide electrical stimulation to the user's muscles to generate stimulated trunk torque in response to signals sent from the one or more communication regional interfaces as directed by the stimulation controller; and wherein the combined flexor righting torque and the stimulated trunk torque combined comprise at least 75% of the user trunk torque when the user's torso is angled from vertical.

* * * * *